Figure 1:
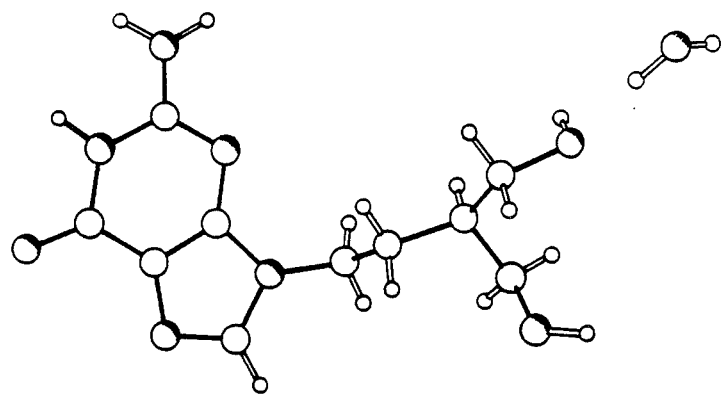

United States Patent [19]

Harnden et al.

[11] Patent Number: 4,942,166

[45] Date of Patent: Jul. 17, 1990

[54] CRYSTALLINE PURINE COMPOUNDS

[75] Inventors: Michael R. Harnden; Richard L. Jarvest; Graham R. Geen, all of Epsom, England

[73] Assignee: Beecham Group p.l.c., Middlesex, England

[21] Appl. No.: 374,628

[22] Filed: Jun. 30, 1989

Related U.S. Application Data

[63] Continuation of Ser. No. 221,894, Jul. 20, 1988, abandoned, which is a continuation of Ser. No. 889,362, Jul. 25, 1986, abandoned.

[30] Foreign Application Priority Data

Jul. 27, 1985 [GB] United Kingdom ............... 8519011
Dec. 11, 1985 [GB] United Kingdom ............... 8530491

[51] Int. Cl.$^5$ .................. C07D 473/18; A61K 31/52
[52] U.S. Cl. .................. 514/262; 514/263; 544/276; 544/277
[58] Field of Search ............... 544/276, 277; 514/262, 514/263

[56] References Cited

U.S. PATENT DOCUMENTS 4,642,346  2/1987  Chan et al. .................. 544/277
4,798,833  1/1989  Johansson et al. ............ 546/277

FOREIGN PATENT DOCUMENTS 0141927  5/1985  European Pat. Off. .
0146516  6/1985  European Pat. Off. .
0152316  8/1985  European Pat. Off. .

*Primary Examiner*—Nicholas S. Rizzo
*Attorney, Agent, or Firm*—Hopgood, Calimafde, Kalil, Blaustein & Judlowe

[57] ABSTRACT

A crystalline monohydrate of the compound of formula (A) or a crystalline sodium salt monohydrate of the compound of formula (A):

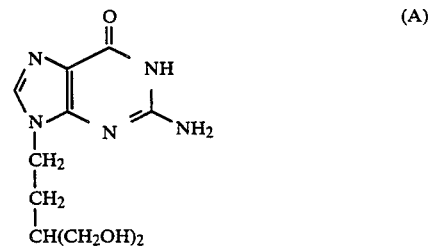

having antiviral activity, processes for their preparation and their use as pharmaceuticals.

8 Claims, 4 Drawing Sheets

CRYSTALLINE PURINE COMPOUNDS

This application is a continuation of application Ser. No. 221,894, filed July 20, 1988, which is a continuation of Ser. No. 889,362, filed July 25, 1986, both now abandoned.

The present invention relates to a novel form of a guanine derivative and a novel form of the sodium salt of the guanine derivative, both having antiviral activity, to a process for their preparation and their use in therapy. EP-A-141927 discloses the compound of formula (A), 9-(4-hydroxy-3-hydroxymethylbut-1-yl) guanine:

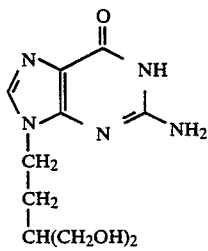

and its sodium salt (in Example 12) and their pharmaceutical use in the treatment of viral infections.

The sodium salt of the compound of formula (A) is preferred for therapeutic use when parenteral administration is desirable, because of its improved solubility over the free base.

It is important, however, that a solid product comprising the compound of formula (A) or its sodium salt should be stable and have good handling qualities for commercial production.

A pure crystalline monohydrate of the compound of formula (A) and of the sodium salt thereof have now been discovered, these hydrates possessing antiviral activity.

These hydrates exist in crystalline form, and have improved stability and handling qualities over the anhydrous forms disclosed in EP-A-141927.

Accordingly the present invention provides a crystalline monohydrate of the compound of formula (A) or a crystalline sodium salt monohydrate of the compound of formula (A).

The invention also provides, in a further particular aspect, a process for the preparation of a crystalline monohydrate of the compound of formula (A) which process comprises dissolving the compound of formula (A) in an aqueous ammonia solution, allowing the ammonia to evaporate off and recovering the crystals so formed.

Preferably the aqueous ammonia solution is a concentrated solution, for example from 5 to 0.5 molar.

The ammoniacal solution of the compound of formula (A) is suitably left to evaporate in moderate temperatures for example from 10 to 70° C. conveniently at ambient temperature for an extended period of time, for example from 1-100 hours, conveniently overnight. Preferably the solution is allowed to stand in well ventilated conditions.

The invention also provides in yet another particular aspect, a further process for the preparation of a crystalline monohydrate of the compound of formula (A) which process comprises suspending the compound of formula (A) in water, adding sodium hydroxide at a non-extreme temperature, bubbling carbon dioxide through the solution, allowing the reaction mixture to stand for a period of time and thereafter recovering the crystals so formed.

The sodium hydroxide is usually added in an amount sufficient to basify the solution to pH 10 to 14, preferably pH 10.5.

The reaction preferably takes place at a temperature of 0 to 30° C., normally at ambient temperature. The solution is allowed to stand for a period of time 1-100 hours, usually overnight.

The crystals of monohydrate may then be filtered off.

In both the above processes, clear orthorhombic crystals of the monohydrate of the compound of formula (A) can be obtained.

Figure 2:
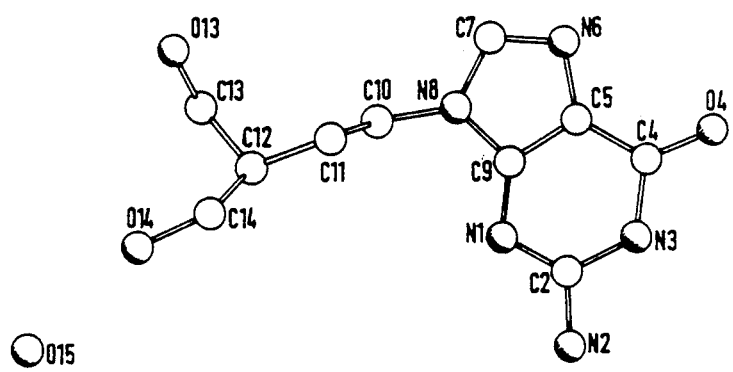

X-ray determination reveals that the crystal has the structure shown in FIGS. 1 and 2.

The compound of formula (A) may be prepared as described in EP-A-141927, preferably in substantially pure anhydrous form.

The invention also provides, in a particular aspect, a process for the preparation of the sodium salt monohydrate of the compound of formula (A), which process comprises dissolving the compound of formula (A) in aqueous sodium hydroxide solution at a non-extreme temperature, removing water by evaporation and recovering the crystals so formed.

The sodium hydroxide is usually in a solution of concentration 0.1 to 5 molar, preferably 0.5 to 0.6 molar.

The solution is allowed to remain at a temperature of 0 to 30° C., normally at ambient temperature 20–25° C., preferably allowing to stand for about an hour.

Preferably the solution is then filtered and the water evaporated under reduced pressure. The crystals may be dried by grinding to a fine powder and drying under reduced pressure over a drying agent such as calcium chloride.

Figure 3:
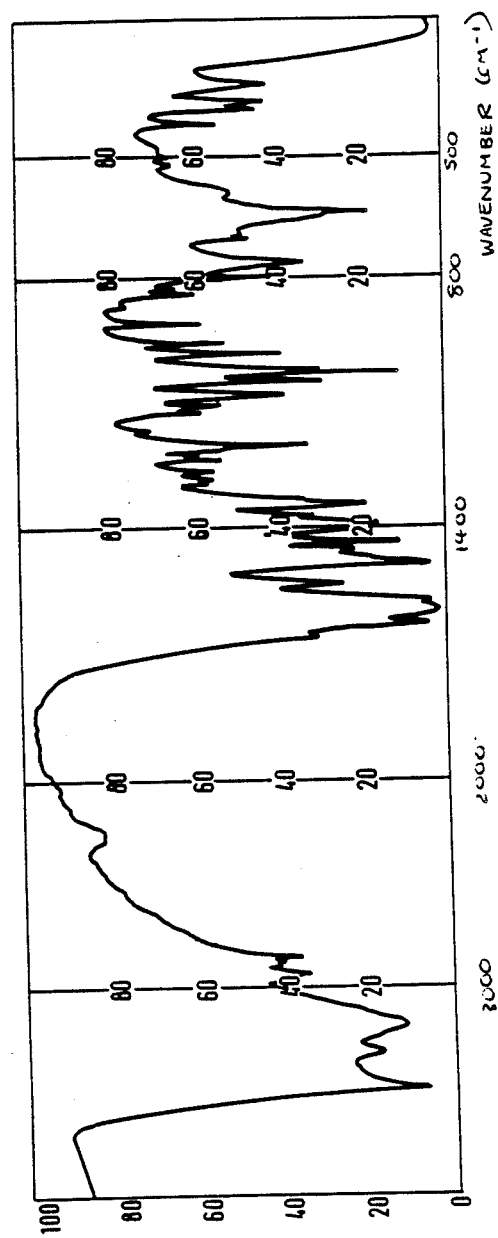
Figure 4:
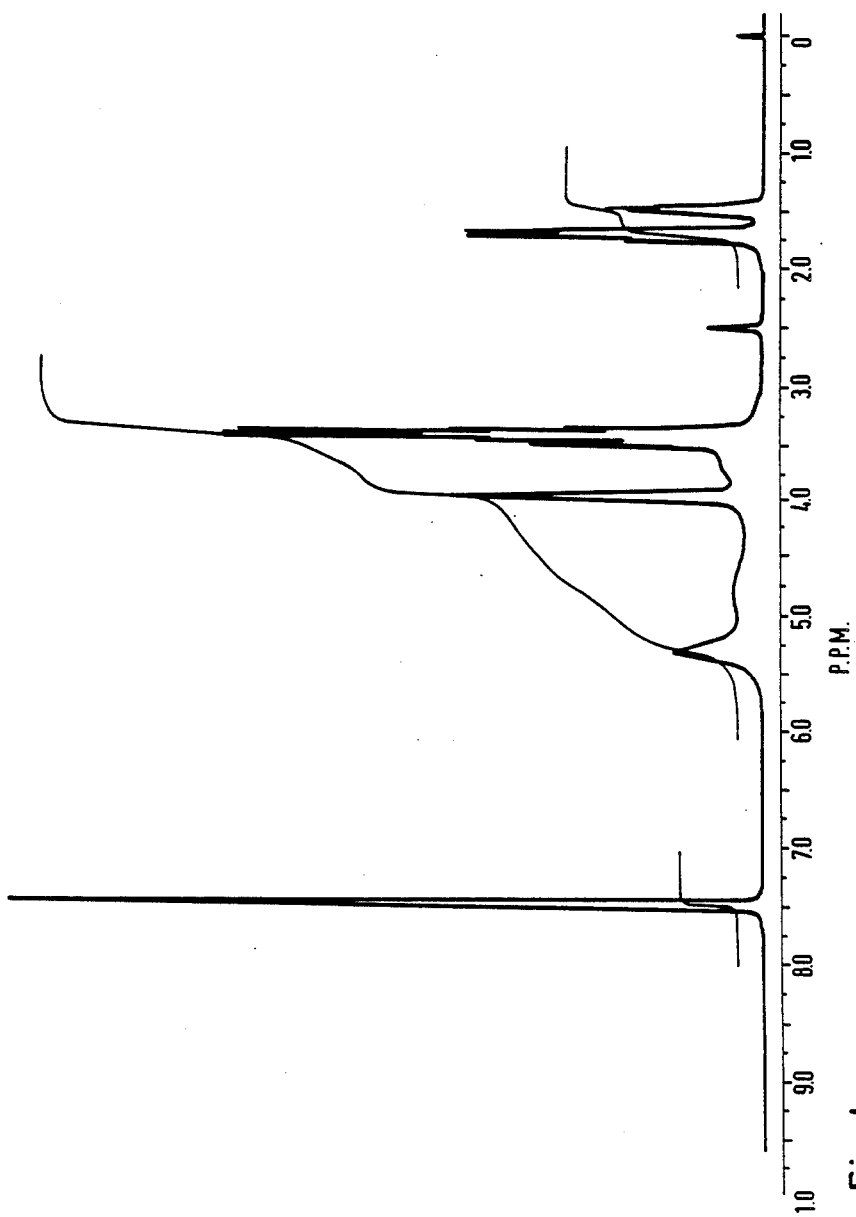
Figure 5:
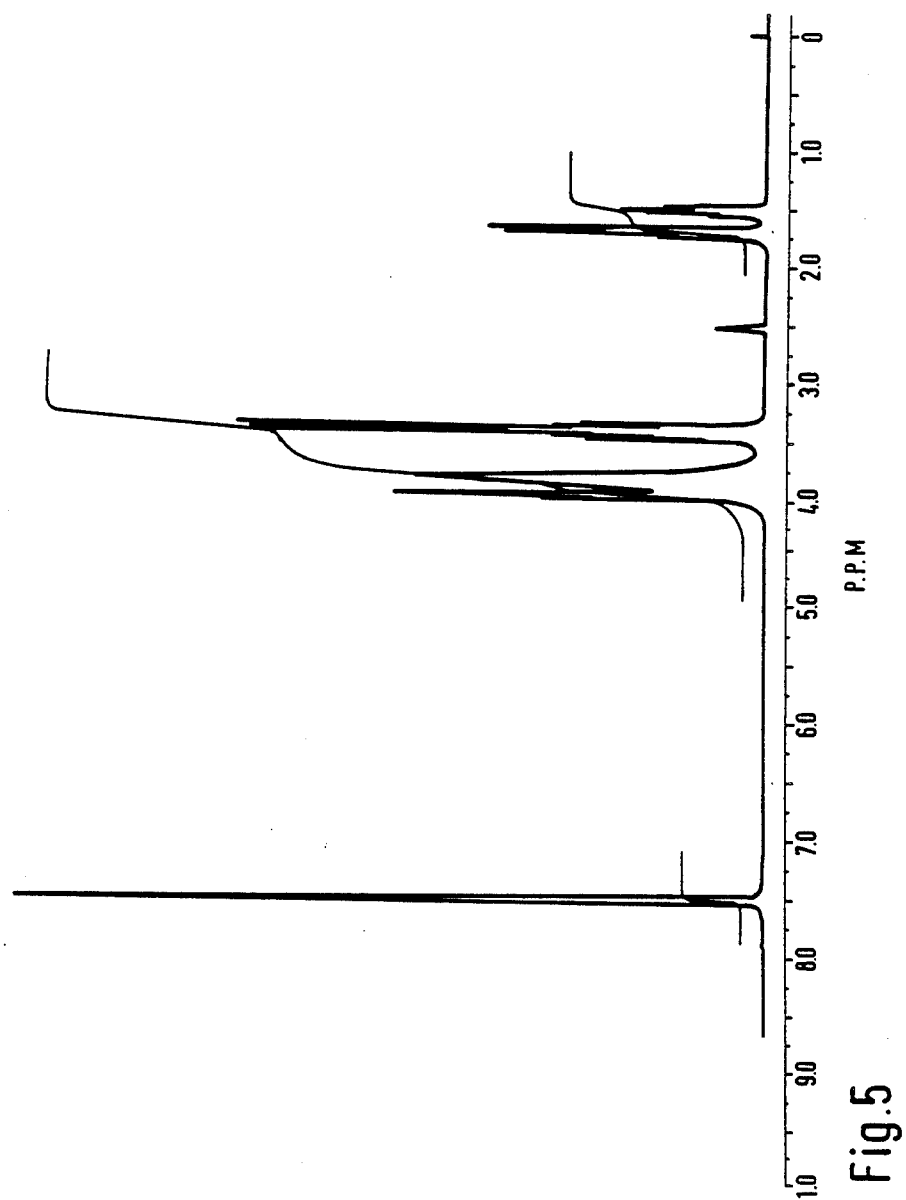

Elemental analysis and other data, such as nmr and IR spectra, shown in FIGS. 3, 4 and 5 confirm that the isolated compound is a monohydrate of the sodium salt of the compound of formula (A).

The sodium salt of the compound of formula (A) may be prepared as described in EP-A-141927, preferably in substantially pure anhydrous form.

The monohydrates may be formulated for use in a pharmaceutical composition for treating viral infections.

The invention further provides a pharmaceutical composition which comprises the monohydrate or the sodium salt monohydrate of the compound of formula (A) together with a pharmaceutically acceptable carrier or excipient.

The compositions may be adapted for administration via the oral, parenteral or topical route, although only the parenteral route is suitable for the sodium salt monohydrate compositions. The compositions of this invention may contain diluents, binder, fillers, disintegrants, lubricants, preservatives in conventional manner.

Compositions suitable for oral administration may be in liquid or solid form.

Solid compositions for oral administration may be in the form of, for example, a capsule, tablet, lozenge, pastille, granule or powder.

Solid oral dosage forms may contain conventional excipients such as diluents, for example lactose, microcrystalline cellulose, dicalcium phosphate, mannitol, magnesium carbonate, glycine, dextrose, sucrose, starch, mannitol, sorbitol and calcium carbonate; binders, for example liquid glucose, syrup, acacia, gelatin, starch mucilage, methylcellulose, polyvinylpyrrolidone, alginates, and pregelatinised starch; disintegrants for example starch, alginic acid, microcrystalline cellulose, pectin, cross-linked polyvinylpyrrolidone, sodium starch glycollate and sodium carboxymethyl-cellulose; glidants for example talc and silica; lubricants for example stearic acid and magnesium stearate; preservatives for example sorbic acid and methyl or propyl parahydroxybenzoate, or pharmaceutically acceptable wetting agents for example sodium lauryl sulphate.

Capsules consist of a shell, normally of gelatin together with other ingredients for example, glycerol, sorbitol, surface-active agents, opaque fillers, preservatives, sweeteners, flavours and colours. The contents of capsules may include diluents, lubricants and disintegrants. Tablets consist of compressed powders or granules, may be coated or uncoated and may be designed so as to dissolve, disperse or effervesce before administration to the patient, or to dissolve or disperse in the gastrointestinal tract either immediately after swallowing, or, in the case of tablets with acid-insoluble coatings, at later times. Tablets usually contain excipients such as diluents, binders, disintegrants, glidants, lubricants and may contain colours and flavours. Effervescent tablets generally contain acids together with carbonates or bicarbonates. Coatings for tablets may consist of natural or synthetic resins, gums, insoluble fillers, sugars, plasticisers, polyhydric alcohols and waxes and may also contain colours and flavours. Lozenges and pastilles are intended to dissolve in the mouth. Lozenges may be moulded or compressed, and usually have a flavoured base. Pastilles are moulded from a base of gelatin and glycerol or acacia and sucrose. They may contain a preservative as well as colours and flavours.

Film-coating resins include zein, vinyl polymers and acrylic resins, and coating compositions usually include plasticisers, such as castor oil or glycerol triacetate. Enteric-coating resins include cellulose acetate phthalate and copolymers of methacrylic acid.

Solid compositions suitable for oral administration may be obtained by conventional methods of blending, filling, granulation, tabletting or the like. Repeated blending operations may be used to distribute the active agent throughout those compositions employing large quantities of fillers.

Liquid compositions suitable for oral administration may be in the form of, for example, elixirs, mixtures, suspensions, emulsions or linctuses. They may be presented as a dry product for reconstitution with water or other suitable vehicle before use. Such liquid compositions may contain conventional excipients such as suspending agents, for example sucrose, sorbitol, gelatin, methyl cellulose, carboxymethlcellulose, hydroxypropyl methyl cellulose, sodium alginate, Xanthan gum, acacia, carageenan, silica, aluminium stearate gel; emulsifying agents, for example lecithin, acacia, sorbitan mono-oleate; aqueous or non-aqueous vehicles which include edible oils, oily esters, for example esters of glycerol, ethanol, glycerol; buffering agents for example citrates and phosphates of alkali metals; preservatives, for example sodium benzoate, sorbic acid, methyl or propyl parahydroxybenzoate; and if desired, conventional flavouring and colouring agents.

Compositions suitable for parenteral administration may be in the form of solutions, suspensions or emulsions, or dry powders which are dissolved or suspended in a suitable vehicle prior to use.

Fluid unit dosage forms are prepared utilising the compound and a pyrogen-free sterile vehicle. The compound, depending on the vehicle and concentration used, can be either dissolved or suspended in the vehicle. Solutions may be used for all forms of parenteral administration, and are particularly used for intravenous infection. In preparing solutions the compound can be dissolved in the vehicle, the solution being made isotonic if necessary by addition of sodium chloride and sterilised by filtration through a sterile filter using aseptic techniques before filling into suitable sterile vials or ampoules and sealing. Alternatively, if solution stability is adequate, the solution in its sealed containers may be sterilised by autoclaving. Advantageously additives such as buffering, solubilising, stabilising, preservative or bactericidal, suspending or emulsifying agents and/or local anaesthetic agents may be dissolved in the vehicle.

Dry powders which are dissolved or suspended in a suitable vehicle prior to use may be prepared by filling pre-sterilised drug substance and other ingredients into a sterile container using aseptic technique in a sterile area. Alternatively the drug and other ingredients may be dissolved in an aqueous vehicle, the solution is sterilised by filtration and distributed into suitable containers using aseptic technique in a sterile area. The product is then freeze dried and the containers are sealed aseptically.

Parenteral suspensions, suitable for intramuscular, subcutaneous or intradermal injection, are prepared in substantially the same manner, except that the sterile compound is suspended in the sterile vehicle, instead of being dissolved and sterilisation cannot be accomplished by filtration. The compound may be isolated in a sterile state or alternatively it may be sterilised after isolation, e.g. by gamma irradiation. Advantageously, a suspending agent for example polyvinylpyrrolidone is included in the composition to facilitate uniform distribution of the compound.

Compositions for topical administration include creams, lotions, liniments, gels, ointments, sprays, tulles, pastes, powders, wound dressings and transdermal devices. These may be produced in a conventional manner, for example, as described in the standard textbooks such as "Dermatological Formulations"—B. W. Barry (Drugs and the Pharmaceutical Sciences—Dekker) or Harrys Cosmeticology (Leonard Hill Books).

The composition can vary from liquid through semi-liquid, semi solid/solid to solid polymeric devices. Examples include ointments, creams, gels, lotions, pastes, powders, liniments for specific localised indications, e.g. ophthalmic delivery systems; nasal ointments; and formulations developed to maximise efficiency in treatment of skin and related diseases.

The product may or may not be sterile, and suitably preserved.

Liquid vehicles can be aqueous or non-aqueous. Suitable non-aqueous vehicles include ethyl alcohol, glycerol, propylene glycol or liquid grades of polyethylene glycol.

Oily components, which may be used in greasy bases or non greasy creams include acceptable fixed oils such as arachis oil, paraffin such as liquid or soft paraffin, and fats of animal origin, such as wool fat. Such compositions may include a suitable emulsifier, for example polyhydric alcohol esters such as sorbitan monostearate, fatty acid salts such as sodium stearate or fatty acid esters such as glyceryl monostearate, as well as thickening and bodying agents as described in various pharmaceutical textbooks, such as 'Modern Pharmaceutics' by Banker and Rhodes.

The compositions may also contain other conventional ingredients such as preservatives, anti-oxidants, film formers, stabilisers, or fragrances. A penetration enhancer such as propylene glycol or dimethyl isosorbide may also be included if it is desired that the active component should penetrate to the systemic system.

Preferably, the composition of this invention is in unit dosage form or in some other suitable form for oral or parenteral administration. A suitable dosage unit might contain from 50 mg to 1 g of active ingredient, for example 100 to 500 mg. Such doses may be administered 1 to 4 times a day or more usually 2 or 3 times a day. The effective dose of compound will in general be in the range of from 1.0 to 20 mg/kg of body weight per day or more usually 2.0 to 10 mg/kg per day. No toxicological effects are indicated at the aforementioned dosage range.

In a further aspect of the invention there is provided a method of treating viral infections in a human or non-human animal, which comprises administering to the animal an effective, non-toxic amount of the monohydrate or the sodium salt monohydrate of the compound of formula (A); and the monohydrate or the sodium salt monohydrate of the compound of formula (A) for use as a pharmaceutical, in particular, for use in the treatment of viral infections.

The following Examples illustrate the invention.

EXAMPLE 1

9-(4-Hydroxy-3-hydroxymethylbut-1-yl)guanine monohydrate. (Method 1)

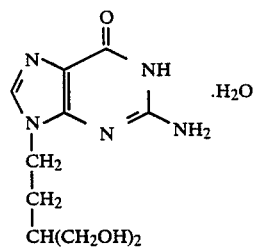

9-(4-Hydroxy-3-hydroxymethylbut-1-yl)guanine (60 mg) was suspended in water (1.8 ml) and concentrated aqueous ammonia (specific gravity 0.88) was added until complete dissolution occured (0.4 ml).

The solution was allowed to stand in a well-ventilated place overnight and then filtered. Clear orthorhombic crystals of 9-(4-hydroxy-3-hydroxymethylbut-1-yl)guanine monohydrate were obtained (m.p.=277° 1 C.).

Crystal Data $C_{10}H_{15}N_5O_3,H_2O$ orthorhombic, a=8.204(1), b=11.016(1), c=13.888(2)A, U=1255A$^3$, space group Pn2,a, z=4, M=271, $D_c$=1.44 gcm$^{-3}$, R=0.030, $R_w$=0.032 for 879 independent observed reflections [$|F_o|>30-(|F_o|)$, $-<58°$, CuKa radiation].

The bond lengths and bond angles, as determined by X-ray crystallography, are given in tables 1 and 2 respectively. The assignment of atoms is shown in FIG. 2.

TABLE 1

| Bond lengths (A) | | | |
|---|---|---|---|
| N(1)-C(2) | 1.328(3) | N(1)-C(9) | 1.355(3) |
| C(2)-N(2) | 1.332(4) | C(2)-N(3) | 1.370(3) |
| N(3)-C(4) | 1.387(4) | C(4)-O(4) | 1.246(3) |
| C(4)-C(5) | 1.405(3) | C(5)-N(6) | 1.374(4) |
| C(5)-C(9) | 1.386(3) | N(6)-C(7) | 1.307(3) |
| C(7)-N(8) | 1.371(3) | N(8)-C(9) | 1.371(3) |
| N(8)-C(10) | 1.470(3) | C(10)-C(11) | 1.503(3) |
| C(11)-C(12) | 1.531(3) | C(12)-C(13) | 1.514(4) |
| C(12)-C(14) | 1.516(4) | C(13)-O(13) | 1.419(4) |
| C(14)-O(14) | 1.428(3) | | |

TABLE 2

| Bond angles (deg.) | | | |
|---|---|---|---|
| C(2)-N(1)-C(9) | 111.8(2) | N(1)-C(2)-N(2) | 120.1(2) |
| N(1)-C(2)-N(3) | 123.9(2) | N(2)-C(2)-N(3) | 116.0(2) |
| C(2)-N(3)-C(4) | 124.9(2) | N(3)-C(4)-O(4) | 119.9(2) |
| N(3)-C(4)-C(5) | 112.3(2) | O(4)-C(4)-C(5) | 127.8(2) |
| C(4)-C(5)-N(6) | 130.3(2) | C(4)-C(5)-C(9) | 118.7(2) |
| N(6)-C(5)-C(9) | 111.0(2) | C(5)-N(6)-C(7) | 104.4(2) |
| N(6)-C(7)-N(8) | 113.1(2) | C(7)-N(8)-C(9) | 106.3(2) |
| C(7)-N(8)-C(10) | 126.3(2) | C(9)-N(8)-C(10) | 127.3(2) |
| N(1)-C(9)-C(5) | 128.3(2) | N(1)-C(9)-N(8) | 126.6(2) |
| C(5)-C(9)-N(8) | 105.1(2) | N(8)-C(10)-C(11) | 113.2(2) |
| C(10)-C(11)-C(12) | 111.5(2) | C(11)-C(12)-C(13) | 114.3(2) |
| C(11)-C(12)-C(14) | 109.2(2) | C(13)-C(12)-C(14) | 111.8(2) |
| C(12)-C(13)-O(13) | 112.0(2) | C(12)-C(14)-O(14) | 113.0(2) |

EXAMPLE 2

(monohydrate preparation Method 2)

9-(4-Hydroxy-3-hydroxymethylbut-1-yl)guanine (3.0 g) was suspended in water (150 ml) and concentrated aqueous ammonia was added until complete dissolution occurred. The solution was allowed to stand in a well ventilated place for 44 h and was then filtered to afford large clear crystals of 9-(4-hydroxy-3-hydroxymethylbut-1yl)guanine monohydrate (2.08 g). Found: C, 44.09; H, 6.33; N, 25.72%. $C_{10}H_{15}N_5O_3.H_2O$ requires C, 44.28; H, 6.32; N, 25.82%. The mother liquor was left for a further 68 h (final pH=9.0) and filtered to give small clear crystals of 9-(4-hydroxy-3-hydroxymethylbut-1yl)guanine monohydrate (0.83 g). Found: C, 44.29; H, 6.27; N, 25.83%. $C_{10}H_{15}N_5O_3.H_2O$ requires C, 44.28; H, 6.32; N, 25.82%. Total 2.91 g, 91%.

EXAMPLE 3

(monohydrate preparation Method 3)

9-(4-Hydroxy-3-hydroxymethylbut-1-yl)guanine (3.0 g) was suspended in water (120 ml) and sodium hydroxide (4.8 g) was added. When complete dissolution had occurred, a stream of air containing carbon dioxide was bubbled through the solution. When the solution started to become cloudy the air flow was stopped and a flocculent white precipitate rapidly appeared. On standing overnight (solution pH=10.5) the precipitate recrystallised and the solution was filtered to afford clear crystals of 9-(4-hydroxy-3-hydroxymethylbut-1-yl) guanine monohydrate (2.5 g, 78%). Found: C, 43.56; H, 6.21; N, 25.40%. $C_{10}H_{15}N_5O_3.H_2O$ requires C, 44.28; H, 6.32; N, 25.82%. Thermogravimetric analysis, found: 6.75% weight loss (90–150° C.); theory for loss of H2O from $C_{10}H_{15}N_5O_3.H_2O$: 6.64% weight loss.

EXAMPLE 4

9-4-(Hydroxy-3-hydroxymethylbut-1-yl)guanine, sodium salt monohydrate

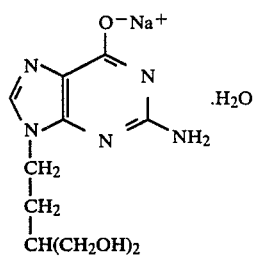

9-(4-Hydroxy-3-hydroxymethylbut-1-yl)guanine (113.8 g) was added to a solution of sodium hydroxide (18.0 g) in water (750 ml) and the solution allowed to remain at 20° C. for 1 hour. The solution was then filtered and the water evaporated under reduced pressure (ca 15 mm Hg). The solid residue was ground to a fine powder and dried under reduced pressure (ca 15 mm Hg) over anhydrous calcium chloride for 3 days, affording the sodium salt monohydrate (130.0 g).

Elemental analysis

Found: C, 40.93; H, 5.27; N, 23.57; Na, 7.54%. Calculated for $C_{10}H_{14}N_5O_3Na.H_2O$: C, 40.95; H, 5.50; N, 23.89; Na, 7.84%.

Water Content (KF-CAO2)

Found: 5.97%; Calculated for $C_{10}H_{14}N_5O_3Na.H_2O$: 6.14%

Thermal Analysis

Broad endotherm, Tp=160° C.; Melting endotherm, Te=266° C.

Spectroscopic Data

IR Spectrum—see FIG. 3. (KBr disc)

$^1H$ nmr Spectrum—see FIGS. 4 and 5. (Solvent - DMSO, 270 MHz). FIG. 5 shows the $^1H$ nmr spectrum with $D_2O$ exchange.

We claim:

1. A crystalline monohydrate of the compound of formula (A) or a crystalline sodium salt monohydrate of the compound of formula (A):

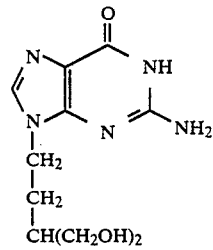

2. The crystalline monohydrate of the compound of formula (A) as defined in claim 1.

3. The crystalline sodium salt monohydrate of the compound of formula (A) as defined in claim 1.

4. A process for the preparation of the crystalline monohydrate of the compound of formula (A) as defined in claim 1, which process comprises dissolving the compound of formula (A) in an aqueous ammonia solution, allowing the ammonia to evaporate off and recovering the crystals so formed.

5. A process for the preparation of the crystalline monohydrate of the compound of formula (A) as defined in claim 1, which process comprises suspending the compound of formula (A) in water, adding sodium hydroxide at a non-extreme temperature, bubbling carbon dioxide through the solution, allowing the mixture to stand for a period of time and thereafter recovering the crystals so formed.

6. A process for the preparation of the sodium salt monohydrate of the compound of formula (A), as defined in claim 1 which process comprises dissolving the compound of formula (A) in aqueous sodium hydroxide solution at a non-extreme temperature, removing water by evaporation and recovering the crystals so formed.

7. An antiviral pharmaceutical composition which comprises an effective amount of the monohydrate or the sodium salt monohydrate of the compound of formula (A), as defined in claim 1, together with a pharmaceutically acceptable carrier or excipient.

8. The method of treatment of viral infections in human and non-human animals, which comprises the administration of effective, non-toxic amount of the monohydrate or the sodium salt monohydrate of the compound of formula (A), as defined in claim 1.

* * * * *